United States Patent [19]

Kaneoya et al.

[11] Patent Number: 5,076,947
[45] Date of Patent: Dec. 31, 1991

[54] 1-PHENYL-1-PROPANOL DERIVATIVE

[75] Inventors: Masakazu Kaneoya; Manabu Uchida; Naoyuki Yoshida; Kazutoshi Miyazawa, all of Ichiharashi, Japan

[73] Assignee: Chisso Corporation, Osaka, Japan

[21] Appl. No.: 361,864

[22] Filed: Jun. 6, 1989

[30] Foreign Application Priority Data

Aug. 8, 1988 [JP] Japan .................. 63-197620

[51] Int. Cl.$^5$ .................. C09K 19/12; C07C 255/00; C07C 69/76
[52] U.S. Cl. .................. 252/299.65; 252/299.61; 252/299.63; 560/59; 560/65; 560/73; 560/102; 558/414; 558/416
[58] Field of Search .................. 252/299.65, 299.01, 252/299.61, 299.63; 560/59, 73, 65, 102; 558/414, 416

[56] References Cited

U.S. PATENT DOCUMENTS

| | | | |
|---|---|---|---|
| 4,764,619 | 8/1988 | Gunjima et al. | 252/299.65 |
| 4,911,863 | 3/1990 | Sage et al. | 252/299.65 |
| 4,965,018 | 10/1990 | Uchida et al. | 252/299.61 |
| 4,988,458 | 1/1991 | Heppke et al. | 252/299.63 |

FOREIGN PATENT DOCUMENTS 8705316  9/1987  World Int. Prop. O. ...... 252/299.61

Primary Examiner—John S. Maples
Assistant Examiner—Philip Tucker
Attorney, Agent, or Firm—Wenderoth, Lind & Ponack

[57] ABSTRACT

An optically active compound having a high twistability and almost no change in the intrinsic pitch depending on temperature, and a liquid crystal composition comprising the compound are provided, which optically active compound is expressed by the formula

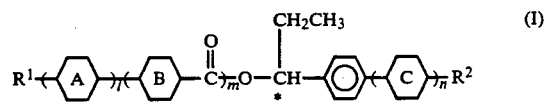

wherein $R^1$ and $R^2$ each represent 1-20C alkyl or alkoxy, halogen or H; l, m and n each represent 0 or 1; and

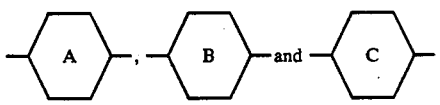

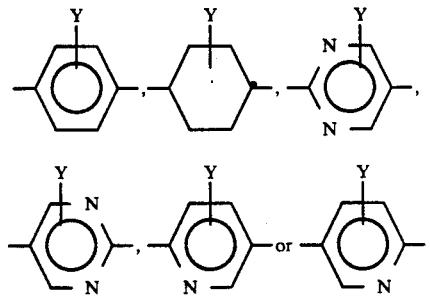

wherein Y represents H, halogen or cyano.

3 Claims, No Drawings

1-PHENYL-1-PROPANOL DERIVATIVE

BACKGROUND OF THE INVENTION

1. Field of the Invention

This invention relates to a novel organic compound and a liquid crystal composition containing the same. More particularly it relates to an organic compound having an optically active group and a liquid crystal composition containing the same.

2. Description of the Related Art

Use applications of liquid crystal display elements have been rapidly expanded due to improvements in circuit, driving mode and cell preparation technique and further, particularly due to improvement in the characteristics of liquid crystal compositions filled in the elements. However, as to liquid crystal display elements, a number of problems to be solved have still been left.

For example, narrow angle of view, inferior contrast, low response rate, still small display capacity, reduction in the display quality due to ambient temperature change, etc. are mentioned. Among these, the reduction in the display quality due to ambient temperature change is caused by temperature change in the threshold voltage Vth.

In recent years, as a means usually employed, there is a method of retaining the display quality by adding a slight quantity of an optically active substance to a liquid crystal composition to inhibit the reverse twist of liquid crystal molecules and thereby impart a right turn or left turn helical structure to the liquid crystal molecules. For example, this method can have an advantageous effect upon the cases of TN (twisted nematic) mode display elements, SBE (supertwisted birefringence effect) mode display elements, etc.

However, if the twistability of an optically active substance added as a dopant is too low, it is required to add the dopant in a relatively high concentration in order to obtain a necessary pitch; hence it is evident this will have a disadvantageous effect upon other substance parameters.

Thus, there has been long awaited an optically active substance having a high twistability i.e,. a capability of exhibiting, when added to liquid crystals, a shorter pitch than those of other substances.

For example, when a commercially available CB-15 made by BDH Co., Ltd. or compounds disclosed in Japanese patent application laid-open Nos. Sho 62-81354/1987 and Sho 62-81355/1987 are added in only one % by weight to nematic liquid crystal compositions, they have a capability of exhibiting a pitch around 10 μm; hence they can be said in a certain sense to be practically usable, optically active substances.

However, when generally known optically active substances, including the above-mentioned compounds, are added, they increase the pitch of liquid crystal substances with temperature rise; hence they often have an undesirable influence upon the liquid crystal substances. For example, in the case of SBE mode, the intrinsic pitch P of liquid crystal compositions varies depending on temperature change, whereby the ratio (P/d) of the intrinsic pitch P of liquid crystal compositions to the cell thickness d of display elements also varies. Usually the P/d is 2 or less, but if it exceeds 2 due to temperature change, 270° twist changes to 90° twist.

Further, in the aspect of improvement for increasing the display capacity, it is necessary to improve the steepness of change in the transmittance when voltage is impressed to display elements. G. Bauer and W. Fehlenbach reported a calculation result that when the twist is changed to 270°, the steepness is improved to a large extent (15th Freiburg Liquid Crystal Meeting (1985)), but in this case, too, it is necessary therefor to be free from change in the intrinsic viscosity depending on temperature (i.e. temperature-dependency of intrinsic pitch).

As to a method for solving this problem, an optically active compound having a negative temperature characteristic i.e., a substance the intrinsic pitch of which decreases with temperature rise, has been found in recent years, and when this substance is mixed in a suitable quantity with a conventional optically active substance having a positive temperature characteristic, a composition having no temperature-dependency of the intrinsic pitch has been obtained (Emoto et al, Japanese patent application No. Sho 61-179194/1986).

However, such a method wherein a compound having a positive temperature characteristic is mixed with a compound having a negative one in a suitable proportion to be free from the temperature-dependency of the intrinsic pitch is very troublesome, and further it is difficult to have a pitch of a necessary length precisely exhibited.

In order to solve these problems, a compound having a short pitch and also having no temperature-dependency of the intrinsic pitch has been desired.

SUMMARY OF THE INVENTION

The present inventors have conducted extensive research in order to obtain an optically active compound having characteristics required for realizing a liquid crystal composition having preferable characteristics as described above, i.e. an optically active compound having a high twistability and also having no temperature-dependency of the intrinsic pitch, and as a result have achieved the present invention.

The present invention resides in
an optically active compound expressed by the formula

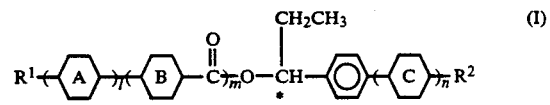

wherein $R^1$ and $R^2$ each represent an alkyl group or an alkoxy group each of 1 to 20 carbon atoms, a halogen atom or hydrogen atom; l, m and n each represent 0 or 1; and

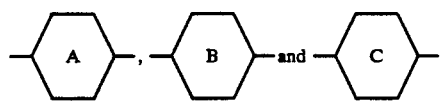

each independently represent

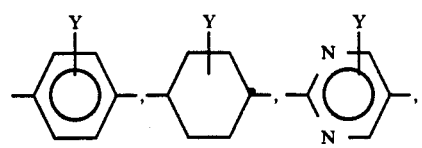

-continued

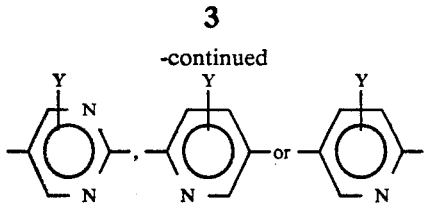

wherein Y represents hydrogen atom, a halogen atom or cyano group,
a liquid crystal composition containing at least one of the above optically active compounds, and
an electrooptical element constituted by using the above liquid crystal composition.

DETAILED DESCRIPTION OF PREFERRED EMBODIMENTS

The compound of the present invention exhibits no liquid crystallinity by itself.

A first specific feature of the compound of the present invention consists in that when it is used as a dopant for liquid crystal compositions, a small quantity of the compound added induces a high twist structure. As shown in Example 2 mentioned later, when the compound is added in 1% by weight to a liquid crystal composition having no twist structure, the resulting pitch is as short as 3.7 μm at 25° C. so that it is possible to prepare a liquid crystal composition having an optimized twist structure, i.e. a chiral liquid crystal composition in a smaller quantity of the compound added.

This is seen to be a surprising specific structure, taking into account the fact that an optically active compound currently known as a dopant, e.g. C-15 (a trade name of product made by BDH Co., Ltd.) affords a pitch of 63 μm, and even CB-15 (a trade name of product made by the Company) affords only 10 μm.

Further, a second specific feature of the compound of the present invention consists in that change in the pitch depending on temperature is very flat. As shown in Example 2, the temperature characteristic δp is as very flat as 0 at $t_1 = 20°$ C. and $t_2 = 60°$ C.; thus it is possible to easily provide a liquid crystal composition having a good temperature characteristic (i.e. a small temperature dependency) of pitch.

Further, since the compound of the present invention has a high twistability, the quantity thereof added which is necessary for obtaining a chiral liquid crystal composition having an optimized twist structure may be small so that it is possible to blend the compound with various kinds of liquid crystal substances. Examples of such liquid crystal substances are Schiff's bases, biphenyls, phenylcyclohexanes, phenylpyridines, phenylpyrimidines, phenyldioxanes, cyclohexylbiphenyls, cinnamic esters, phenyl esters, etc. and liquid crystal compositions obtained by combining compounds optionally chosen from among the foregoing compounds.

Further, chiral liquid crystal compositions obtained by adding the compound of the present invention, i.e. liquid crystal compositions having a twist structure, are not limited only to chiral nematic compositions, but also refer to compositions having chiral smectic C phase, having a twist structure had in smectic phase, particularly smectic C phase. In recent years, research on a novel drive mode utilizing chiral smectic C phase has been extensively conducted (Clark et al: Applied Phys. lett., 36, 899 (1980)) and when the compound of the present invention is added to a compound or a composition having smectic C phase, it is possible to induce chiral smectic C phase.

The superior specific features of the compound of the present invention as described above are considered to originate from the central core of the chemical structure of the compound, i.e.

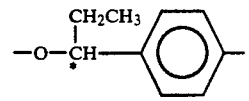

and with regard to the structures on both sides of the above core, the specific features are not restricted thereby so much, as expressed by the above formula (I).

Names of concrete compounds preferred among those of the present invention will be enumerated below:

optically active 4-methylbenzoic acid 1-phenyl-1-propyl ester
optically active 4-ethylbenzoic acid 1-phenyl-1-propyl ester
optically active 4-propylbenzoic acid 1-phenyl-1-propyl ester
optically active 4-butylbenzoic acid 1-phenyl-1-propyl ester
optically active 4-hexylbenzoic acid 1-phenyl-1-propyl ester
optically active 4-heptylbenzoic acid 1-phenyl-1-propyl ester
optically active 4-nonylbenzoic acid 1-phenyl-1-propyl ester
optically active 4-decylbenzoic acid 1-phenyl-1-propyl ester
optically active 4-ethyloxybenzoic acid 1-phenyl-1-propyl ester
optically active 4-pentyloxybenzoic acid 1-phenyl-1-propyl ester
optically active 4-octyloxybenzoic acid 1-phenyl-1-propyl ester
optically active 4-chlorobenzoic acid 1-phenyl-1-propyl ester
optically active 4-bromobenzoic acid 1-phenyl-1-propyl ester
optically active 4-fluorobenzoic acid 1-phenyl-1-propyl ester
optically active 4-cyanobenzoic acid 1-phenyl-1-propyl ester
optically active 2-fluorobenzoic acid 1-phenyl-1-propyl ester
optically active 2-cyanobenzoic acid 1-phenyl-1-propyl ester
optically active 3-fluorobenzoic acid 1-phenyl-1-propyl ester
optically active 3-cyanobenzoic acid 1-phenyl-1-propyl ester
optically active 4-ethylbenzoic acid 1-(4-methylphenyl)-1-propyl ester
optically active 4-pentylbenzoic acid 1-(4-pentylphenyl)-1-propyl ester
optically active 4-heptylbenzoic acid 1-(4-ethylphenyl)-1-propyl ester
optically active 4-decylbenzoic acid 1-(4-propyloxyphenyl)-1-propyl ester
optically active 4-undecylbenzoic acid 1-(4-butyloxyphenyl)-1-propyl ester optically active 4-dodecylbenzoic acid 1-(4-hexyloxyphenyl)-1-propyl ester
optically active 4-methyloxybenozic acid 1-(4-butylphenyl)-1-propyl ester
optically active 4-propyloxybenzoic acid 1-(4-pentylphenyl)-1-propyl ester
optically active 4-pentyloxybenzoic acid 1-(4-hexyloxyphenyl)-1-propyl ester
optically active 4-pentyloxybenzoic acid 1-(4-fluorophenyl)-1-propyl ester
optically active 4-pentyloxybenzoic acid 1-(4-cyanophenyl)-1-propyl ester
optically active 4-fluorobenzoic acid 1-(4-methylphenyl)-1-propyl ester
optically active 4-cyanobenzoic acid 1-(4-ethylphenyl)-1-propyl ester
optically active 4-fluorobenzoic acid 1-(4-butyloxyphenyl)-1-propyl ester
optically active 4-cyanobenzoic acid 1-(4-pentyloxyphenyl)-1-propyl ester
optically active 4-cyanobenzoic acid 1-(4-cyanophenyl)-1-propyl ester
optically active 2-fluoro-4-butylbenzoic acid 1-phenyl-1-propyl ester
optically active 2-fluoro-4-hexylbenzoic acid 1-phenyl-1-propyl ester
optically active 2-cyano-4-pentylbenzoic acid 1-phenyl-1-propyl ester
optically active 2-cyano-4-octylbenzoic acid 1-phenyl-1-propyl ester
optically active 2-fluoro-4-propyloxybenzoic acid 1-phenyl-1-propyl ester
optically active 2-fluoro-4-heptyloxybenzoic acid 1-phenyl-1-propyl ester
optically active 2-cyano4-butyloxybenzoic acid 1-phenyl-1-propyl ester
optically active 2-cyano-4-nonyloxybenzoic acid 1-phenyl-1-propyl ester
optically active 3-fluoro-4-ethylbenzoic acid 1-phenyl-1-propyl ester
optically active 3-fluoro-4-pentylbenzoic acid 1-phenyl-1-propyl ester
optically active 3-fluoro-4-heptylbenzoic acid 1-phenyl-1-propyl ester
optically active 3-cyano-4-propylbenzoic acid 1-phenyl-1-propyl ester
optically active 3-cyano-4-hexylbenzoic acid 1-phenyl-1-propyl ester
optically active 3-cyano-4-nonylbenzoic acid 1-phenyl-1-propyl ester
optically active 3-fluoro-4-propyloxybenzoic acid 1-phenyl-1-propyl ester
optically active 3-fluoro-4-pentyloxybenzoic acid 1-phenyl-1-propyl ester
optically active 3-fluoro-4-octyloxybenzoic acid 1-phenyl-1-propyl ester
optically active 3-cyano-4-mehtyloxybenzoic acid 1-phenyl-1-propyl ester
optically active 3-cyano-4-pentyloxybenzoic acid 1-phenyl-1-propyl ester
optically active 3-cyano-4-decyloxybenzoic acid 1-phenyl-1-propyl ester
optically active 2-fluoro-4-methylbenzoic acid 1-(4-pentylphenyl)-1-propyl ester
optically active 2-fluoro-4-butylbenzoic acid 1-(4-heptylphenyl)-1-propyl ester
optically active 2-fluoro-4-hexylbenzoic acid 1-(4-nonylphenyl)-1-propyl ester
optically active 2-fluoro-4-ethyloxybenzoic acid 1-(4-butylphenyl)-1-propyl ester
optically active 2-fluoro-4-pentyloxybenzoic acid 1-(4-nonylphenyl)-1-propyl ester
optically active 2-fluoro-4-octyloxybenzoic acid 1-(4-pentyloxyphenyl)-1-propyl ester
optically active 2-cyano-4-pentylbenzoic acid 1-(4-ethylphenyl)-1-propyl ester
optically active 2-cyano-4-hexylbenzoic acid 1-(4-pentylphenyl)-1-propyl ester
optically active 2-cyano-4-pentyloxybenzoic acid 1-(4-ethylphenyl)-1-propyl ester
optically active 2-cyano-4-hexyloxybenzoic acid 1-(4-pentylphenyl)-1-propyl ester
optically active 2-cyano-4-hexylbenzoic acid 1-(4-pentyloxyphenyl)-1-propyl ester
optically active 2-cyano-4-hexylbenzoic acid 1-(4-pentyloxyphenyl)-1-propyl ester
optically active 2-cyano-4-hexyloxybenzoic acid 1-(4-pentyloxyphenyl)-1-propyl ester
optically active 4-methylcyclohexylcarboxylic acid 1-phenyl-1-propyl ester
optically active 4-ethylcyclohexylcarboxylic acid 1-phenyl-1-propyl ester
optically active 4-butylcyclohexylcarboxylic acid 1-phenyl-1-propyl ester
optically active 4-pentylcyclohexylcarboxylic acid 1-phenyl-1-propyl ester
optically active 4-octylcyclohexylcarboxylic acid 1-phenyl-1-propyl ester
optically active 4-decylcyclohexylcarboxylic acid 1-phenyl-1-propyl ester
optically active 4-propyloxycyclohexylcarboxylic acid 1-phenyl-1-propyl ester
optically active 4-hexyloxycyclohexylcarboxylic acid 1-phenyl-1-propyl ester
optically active 4-heptyloxycyclohexylcarboxylic acid 1-phenyl-1-propyl ester
optically active 4-undecyloxycyclohexylcarboxylic acid 1-phenyl-1-propyl ester
optically active 4-tridecyloxycyclohexylcarboxylic acid 1-phenyl-1-propyl ester
optically active 4-ethylcyclohexylcarboxylic acid 1-(4-pentylphenyl)-1-propyl ester
optically active 4-butylcyclohexylcarboxylic acid 1-(4-pentylphenyl)-1-propyl ester
optically active 4-pentylcyclohexylcarboxylic acid 1-(4-hexylphenyl)-1-propyl ester
optically active 4-pentylcyclohexylcarboxylic acid 1-(4-hexyloxyphenyl)-1-propyl ester
optically active 4-hexylcyclohexylcarboxylic acid 1-(4-butylphenyl)-1-propyl ester
optically active 4-hexylcyclohexylcarboxylic acid 1-(4-butyloxyphenyl)-1-propyl ester
optically active 4-octylcyclohexylcarboxylic acid 1-(4-nonylphenyl)-1-propyl ester
optically active 4-ethyloxycyclohexylcarboxylic acid 1-(4-methylphenyl)-1-propyl ester
optically active 4-butyloxycyclohexylcarboxylic acid 1-(4-decylphenyl)-1-propyl ester
optically active 4-pentyloxycyclohexylcarboxylic acid 1-(4-butylphenyl)-1-propyl ester
optically active 4-pentyloxycyclohexylcarboxylic acid 1-(4-butyloxyphenyl)-1-propyl ester
optically active 4-hexyloxycyclohexylcarboxylic acid 1-(4-pentylphenyl)-1-propyl ester
optically active 4-hexyloxycyclohexylcarboxylic acid 1-(4-pentyloxyphenyl)-1-propyl ester optically active 4-octyloxycyclohexylcarboxylic acid 1-(4-octylphenyl)-1-propyl ester
optically active 4-nonyloxycyclohexylcarboxylic acid 1-(4-ethylphenyl)-1-propyl ester
optically active 2-ethylpyrimidine-5-carboxylic acid 1-phenyl-1-propyl ester
optically active 2-butylpyrimidine-5-carboxylic acid 1-phenyl-1-propyl ester
optically active 2-pentylpyrimidine-5-carboxylic acid 1-phenyl-1-propyl ester
optically active 2-hexylpyrimidine-5-carboxylic acid 1-phenyl-1-propyl ester
optically active 2-hexyloxypyrimidine-5-carboxylic acid 1-phenyl-1-propyl ester
optically active 2-heptylpyrimidine-5-carboxylic acid 1-phenyl-1-propyl ester
optically active 2-heptyloxypyrimidine-5-carboxylic acid 1-phenyl-1-propyl ester
optically active 2-octylpyrimidine-5-carboxylic acid 1-phenyl-1-propyl ester
optically active 2-octyloxypyrimidine-5-carboxylic acid 1-phenyl-1-propyl ester
optically active 2-decylpyrimidine-5-carboxylic acid 1-phenyl-1-propyl ester
optically active 2-dodecyloxypyrimidine-5-carboxylic acid 1-phenyl-1-propyl ester
optically active 2-methylpyrimidine-5-carboxylic acid 1-(4-ethylphenyl)-1-propyl ester
optically active 2-ethylpyrimidine-5-carboxylic acid 1-(4-butylphenyl)-1-propyl ester
optically active 2-butylpyrimidine-5-carboxylic acid 1-(4-butylphenyl)-1-propyl ester
optically active 2-butylpyrimidine-5-carboxylic acid 1-(4-butyloxyphenyl)-1-propyl ester
optically active 2-butylpyrimidine-5-carboxylic acid 1-(4-pentylphenyl)-1-propyl ester
optically active 2-butylpyrimidine-5-carboxylic acid 1-(4-pentyloxyphenyl)-1-propyl ester
optically active 2-pentylpyrimidine-5-carboxylic acid 1-(4-propylphenyl)-1-propyl ester
optically active 2-pentylpyrimidine-5-carboxylic acid 1-(4-propyloxyphenyl)-1-propyl ester
optically active 2-pentylpyrimidine-5-carboxylic acid 1-(4-hexyloxyphenyl)-1-propyl ester
optically active 2-hexylpyrimidine-5-carboxylic acid 1-(4-ethyloxyphenyl)-1-propyl ester
optically active 2-hexylpyrimidine-5-carboxylic acid 1-(4-butylphenyl)-1-propyl ester
optically active 2-octylpyrimidine-5-carboxylic acid 1-(4-ethylphenyl)-1-propyl ester
optically active 2-octylpyrimidine-5-carboxylic acid 1-(4-propyloxyphenyl)-1-propyl ester
optically active 2-nonylpyrimidine-5-carboxylic acid 1-(4-nonylphenyl)-1-propyl ester
optically active 2-decylpyrimidine-5-carboxylic acid 1-(4-pentylphenyl)-1-propyl ester
optically active 2-decylpyrimidine-5-carboxylic acid 1-(4-hexyloxyphenyl)-1-propyl ester
optically active 5-methylpyrimidine-2-carboxylic acid 1-phenyl-1-propyl ester
optically active 5-propylpyrimidine-2-carboxylic acid 1-phenyl-1-propyl ester
optically active 5-butylpyrimidine-2-carboxylic acid 1-phenyl-1-propyl ester
optically active 5-pentylpyrimidine-2-carboxylic acid 1-phenyl-1-propyl ester
optically active 5-hexylpyrimidine-2-carboxylic acid 1-phenyl-1-propyl ester
optically active 5-heptylpyrimidine-2-carboxylic acid 1-phenyl-1-propyl ester
optically active 5-octylpyrimidine-2-carboxylic acid 1-phenyl-1-propyl ester
optically active 5-nonylpyrimidine-2-carboxylic acid 1-phenyl-1-propyl ester
optically active 5-decylpyrimidine-2-carboxylic acid 1-phenyl-1-propyl ester
optically active 5-undecylpyrimidine-2-carboxylic acid 1-phenyl-1-propyl ester
optically active 5-dodecylpyrimidine-2-carboxylic acid 1-phenyl-1-propyl ester
optically active 5-ethylpyrimidine-2-carboxylic acid 1-(4-propylphenyl)-1-propyl ester
optically active 5-ethylpyrimidine-2-carboxylic acid 1-(4-octylphenyl)-1-propyl ester
optically active 5-propylpyrimidine-2-carboxylic acid 1-(4-pentylphenyl)-1-propyl ester
optically active 5-propylpyrimidine-2-carboxylic acid 1-(4-pentyloxyphenyl)-1-propyl ester
optically active 5-butylpyrimidine-2-carboxylic acid 1-(4-pentylphenyl)-1-propyl ester
optically active 5-butylpyrimidine-2-carboxylic acid 1-(4-pentyloxyphenyl)-1-propyl ester
optically active 5-butyloxypyrimidine-2-carboxylic acid 1-(4-hexylphenyl)-1-propyl ester
optically active 5-pentylpyrimidine-2-carboxylic acid 1-(4-butylphenyl)-1-propyl ester
optically active 5-pentylpyrimidine-2-carboxylic acid 1-(4-butyloxyphenyl)-1-propyl ester
optically active 5-pentyloxypyrimidine-2-carboxylic acid 1-(4-hexylphenyl)-1-propyl ester
optically active 5-pentyloxypyrimidine-2-carboxylic acid 1-(4-heptyloxyphenyl)-1-propyl ester
optically active 5-hexylpyrimidine-2-carboxylic acid 1-(4-ethylphenyl)-1-propyl ester
optically active 5-hexyloxypyrimidine-2-carboxylic acid 1-(4-ethyloxyphenyl)-1-propyl ester
optically active 5-heptylpyrimidine-2-carboxylic acid 1-(4-butylphenyl)-1-propyl ester
optically active 5-heptyloxypyrimidine-2-carboxylic acid 1-(4-pentylphenyl)-1-propyl ester
optically active 5-octylpyrimidine-2-carboxylic acid 1-(4-propylphenyl)-1-propyl ester
optically active 2-ethylpyridine-5-carboxylic acid 1-phenyl-1-propyl ester
optically active 2-ethyloxypyridine-5-carboxylic acid 1-phenyl-1-propyl ester
optically active 2-propylpyridine-5-carboxylic acid 1-phenyl-1-propyl ester
optically active 2-pentylpyridine-5-carboxylic acid 1-phenyl-1-propyl ester
optically active 2-pentyloxypyridine-5-carboxylic acid 1-phenyl-1-propyl ester
optically active 2-hexylpyridine-5-carboxylic acid 1-phenyl-1-propyl ester
optically active 2-hexyloxypyridine-5-carboxylic acid 1-phenyl-1-propyl ester
optically active 2-heptylpyridine-5-carboxylic acid 1-phenyl-1-propyl ester
optically active 2-heptyloxypyridine-5-carboxylic acid 1-phenyl-1-propyl ester
optically active 2-octylpyridine-5-carboxylic acid 1-phenyl-1-propyl ester
optically active 2-decylpyridine-5-carboxylic acid 1-phenyl-1-propyl ester
optically active 2-ethylpyridine-5-carboxylic acid 1-(4-pentylphenyl)-1-propyl ester optically active 2-butylpyridine-5-carboxylic acid 1-(4-pentyloxyphenyl)-1-propyl ester optically active 2-butyloxypyridine-5-carboxylic acid 1-(4-hexylphenyl)-1-propyl ester optically active 2-pentylpyridine-5-carboxylic acid 1-(4-methylphenyl)-1-propyl ester optically active 2-pentyloxypyridine-5-carboxylic acid 1-(4-propylphenyl)-1-propyl ester optically active 2-pentyloxypyridine-5-carboxylic acid 1-(4-pentylphenyl)-1-propyl ester optically active 2-hexylpyridine-5-carboxylic acid 1-(4-butylphenyl)-1-propyl ester optically active 2-hexylpyridine-5-carboxylic acid 1-(4-hexylphenyl)-1-propyl ester optically active 2-hexyloxypyridine-5-carboxylic acid 1-(4-nonylphenyl)-1-propyl ester optically active 2-hexyloxypyridine-5-carboxylic acid 1-(4-decylphenyl)-1-propyl ester optically active 2-heptylpyridine-5-carboxylic acid 1-(4-butylphenyl)-1-propyl ester optically active 2-heptylpyridine-5-carboxylic acid 1-(4-butyloxyphenyl)-1-propyl ester optically active 2-heptyloxypyridine-5-carboxylic acid 1-(4-pentylphenyl)-1-propyl ester optically active 2-heptyloxypyridine-5-carboxylic acid 1-(4-pentyloxyphenyl)-1-propyl ester optically active 2-octylpyridine-5-carboxylic acid 1-(4-pentylphenyl)-1-propyl ester optically active 2-nonylpyridine-5-carboxylic acid 1-(4-ethyloxyphenyl)-1-propyl ester optically active 5-propylpyridine-2-carboxylic acid 1-phenyl-1-propyl ester optically active 5-pentylpyridine-2-carboxylic acid 1-phenyl-1-propyl ester optically active 5-hexylpyridine-2-carboxylic acid 1-phenyl-1-propyl ester optically active 5-heptylpyridine-2-carboxylic acid 1-phenyl-1-propyl ester optically active 5-octylpyridine-2-carboxylic acid 1-phenyl-1-propyl ester optically active 5-nonylpyridine-2-carboxylic acid 1-phenyl-1-propyl ester optically active 5-propyloxypyridine-2-carboxylic acid 1-phenyl-1-propyl ester optically active 5-butyloxypyridine-2-carboxylic acid 1-phenyl-1-propyl ester optically active 5-hexyloxypyridine-2-carboxylic acid 1-phenyl-1-propyl ester optically active 5-heptyloxypyridine-2-carboxylic acid 1-phenyl-1-propyl ester optically active 5-nonyloxypyridine-2-carboxylic acid 1-phenyl-1-propyl ester optically active 5-ethylpyridine-2-carboxylic acid 1-(4-hexylphenyl)-1-propyl ester optically active 5-propylpyridine-2-carboxylic acid 1-(4-hexylphenyl)-1-propyl ester optically active 5-propyloxypyridine-2-carboxylic acid 1-(4-decylphenyl)-1-propyl ester optically active 5-butylpyridine-2-carboxylic acid 1-(4-pentylphenyl)-1-propyl ester optically active 5-butylpyridine-2-carboxylic acid 1-(4-pentyloxyphenyl)-1-propyl ester optically active 5-butyloxypyridine-2-carboxylic acid 1-(4-nonylphenyl)1-lpropyl ester optically active 5-butyloxypyridine-2-carboxylic acid 1-(4-decylphenyl)-1-propyl ester optically active 5-pentylpyridine-2-carboxylic acid 1-(4-octylphenyl)-1-propyl ester optically active 5-pentyloxypyridine-2-carboxylic acid 1-(4-octylphenyl)-1-propyl ester optically active 5-hexylpyridine-2-carboxylic acid 1-(4-propylphenyl)-1-propyl ester optically active 5-hexylpyridine-2-carboxylic acid 1-(4-heptylphenyl)-1-propyl ester optically active 5-hexyloxypyridine-2-carboxylic acid 1-(4-octylphenyl)-1-propyl ester optically active 5-hexyloxypyridine-2-carboxylic acid 1-(4-nonyloxyphenyl)-1-propyl ester optically active 5-heptylpyridine-2-carboxylic acid 1-(4-nonylphenyl)-1-propyl ester optically active 5-heptyloxypyridine-2-carboxylic acid 1-(4-decylphenyl)-1-propyl ester optically active 5-octylpyridine-2-carboxylic acid 1-(4-butylphenyl)-1-propyl ester optically active 4-butylbenzoic acid 1-(4-pentyl-4′-biphenylyl)-1-propyl ester optically active 4-pentylbenzoic acid 1-(4-pentyl-4′-biphenylyl)-1-propyl ester optically active 4-pentylbenzoic acid 1-(4-pentyloxy-4′-biphenylyl)-1-propyl ester optically active 4-hexylbenzoic acid 1-(4-butyl-4′-biphenylyl)-1-propyl ester optically active 4-hexylbenzoic acid 1-(4-nonyl-4′-biphenylyl)-1-propyl ester optically active 4-hexyloxybenzoic acid 1-(4-pentyloxy-4′-biphenylyl)-1-propyl ester optically active 4-heptylbenzoic acid 1-(4-propyl-4′-biphenylyl)-1-propyl ester optically active 4-heptylbenzoic acid 1-(4-butyloxy-4′-biphenylyl)-1-propyl ester optically active 4-heptyloxybenzoic acid 1-(4-hexyl-4′-biphenylyl)-1-propyl ester optically active 4-octylbenzoic acid 1-(4-nonyl-4′-biphenylyl)-1-propyl ester optically active 4-octylbenzoic acid 1-(4-decyl-4′-biphenylyl)-1-propyl ester optically active 3-fluoro-4-pentylbenzoic acid 1-(4-hexyl-4′-biphenylyl)-1-propyl ester optically active 3-fluoro-4-hexyloxybenzoic acid 1-(4-propyl-4′-biphenylyl)-1-propyl ester optically active 3-fluoro-4-octylbenzoic acid 1-(4-pentyl-4′-biphenylyl)-1-propyl ester optically active 3-cyano-4-butylbenzoic acid 1-(4-propyl-4′-biphenylyl)-1-propyl ester optically active 3-cyano-4-butyloxybenzoic acid 1-(4-pentyl-4′-biphenylyl)-1-propyl ester optically active 3-cyano-4-nonylbenzoic acid 1-(4-hexyloxy-4′-biphenylyl)-1-propyl ester optically active 3-cyano-4-decyloxybenzoic acid 1-(4-octyl-4′-biphenylyl)-1-propyl ester optically active 2-butylpyrimidine-5-carboxylic acid 1-(4-butyl-4′-biphenylyl)-1-propyl ester optically active 2-pentylpyrimidine-5-carboxylic acid 1-(4-nonyl-4′-biphenylyl)-1-propyl ester optically active 2-pentyloxypyrimidine-5-carboxylic acid 1-(4-pentyl-4′-biphenylyl)-1-propyl ester optically active 2-hexylpyrimidine-5-carboxylic acid 1-(4-propyl-4′-biphenylyl)-1-propyl ester optically active 2-hexylpyrimidine-5-carboxylic acid 1-(4-pentyloxy-4′-biphenylyl)-1-propyl ester optically active 2-octylpyrimidine-5-carboxylic acid 1-(4-nonyl-4′-biphenyl)-1-propyl ester optically active 2-octyloxypyrimidine-5-carboxylic acid 1-(4-decyl-4′-biphenylyl)-1-propyl ester optically active 2-nonylpyridine-5-carboxylic acid 1-(4-methyl-4'-biphenylyl)-1-propyl ester
optically active 5-pentylpyrimidine-2-carboxylic acid 1-(4-methyl-4'-biphenylyl)-1-propyl ester
optically active 5-pentylpyrimidine-2-carboxylic acid 1-(4-ethyl-4'-biphenylyl)-1-propyl ester
optically active 5-pentyloxypyrimidine-2-carboxylic acid 1-(4-propyl-4'-biphenyl)-1-propyl ester
optically active 5-hexylpyrimidine-2-carboxylic acid 1-(4-propyl-4'-biphenyl)-1-propyl ester
optically active 5-hexylpyrimidine-2-carboxylic acid 1-(4-pentyl-4'-biphenylyl)-1-propyl ester
optically active 5-heptylpyrimidine-2-carboxylic acid 1-(4-pentyloxy-4'-biphenylyl)-1-propyl ester
optically active 5-heptylpyrimidine-2-carboxylic acid 1-(4-hexyl-4'-biphenylyl)-1-propyl ester
optically active 5-heptyloxypyrimidine-2-carboxylic acid 1-(4-nonyl-4'-biphenyl)-1-propyl ester
optically active 5-octylpyrimidine-2-carboxylic acid 1-(4-nonyloxy-4'-biphenyl)-1-propyl ester
optically active 2-butylpyridine-5-carboxylic acid 1-(4-butyl-4'-biphenylyl)-1-propyl ester
optically active 2-pentylpyridine-5-carboxylic acid 1-(4-nonyl-4'-biphenylyl)-1-propyl ester
optically active 2-pentyloxypyridine-5-carboxylic acid 1-(4-pentyl-4'-biphenylyl)-1-propyl ester
optically active 2-hexylpyridine-5-carboxylic acid 1-(4-propyl-4'-biphenylyl)-1-propyl ester
optically active 2-hexylpyridine-5-carboxylic acid 1-(4-pentyloxy-4'-biphenylyl)-1-propyl ester
optically active 2-octylpyridine-5-carboxylic acid 1-(4-nonyl-4'-biphenylyl)-1-propyl ester
optically active 2-octyloxypyridine-5-carboxylic acid 1-(4-decyl-4'-biphenylyl)-1-propyl ester
optically active 2-nonylpyridine-5-carboxylic acid 1-(4-methyl-4'-biphenylyl)-1-propyl ester
optically active 5-pentylpyridine-2-carboxylic acid 1-(4-methyl-4'-biphenylyl)-1-propyl ester
optically active 5-pentylpyridine-2-carboxylic acid 1-(4-ethyl-4'-biphenylyl)-1-propyl ester
optically active 5-pentyloxypyridine-2-carboxylic acid 1-(4-propyl-4'-biphenylyl)-1-propyl ester
optically active 5-hexylpyridine-2-carboxylic acid 1-(4-propyl-4'-biphenylyl)-1-propyl ester
optically active 5-hexylpyridine-2-carboxylic acid 1-(4-pentyl-4'-biphenylyl)-1-propyl ester
optically active 5-heptylpyridine-2-carboxylic acid 1-(4-pentyloxy-4'-biphenylyl)-1-propyl ester
optically active 5-heptylpyridine-2-carboxylic acid 1-(4-hexyl-4'-biphenylyl)-1-propyl ester
optically active 5-heptyloxypyridine-2-carboxylic acid 1-(4-nonyl-4'-biphenylyl)-1-propyl ester
optically active 5-octylpyridine-2-carboxylic acid 1-(4-nonyloxy-4'-biphenylyl)-1-propyl ester
optically active 4-butylcyclohexylcarboxylic acid 1-(4-propyl-4'-biphenylyl)-1-propyl ester
optically active 4-pentylcyclohexylcarboxylic acid 1-(4-propyl-4'-biphenylyl)-1-propyl ester
optically active 4-hexylcyclohexylcarboxylic acid 1-(4-pentyl-4'-biphenylyl)-1-propyl ester
optically active 4-heptylcyclohexylcarboxylic acid 1-(4-pentyloxy-4'-biphenylyl)-1-propyl ester
optically active 4-octylcyclohexylcarboxylic acid 1-(4-hexyl-4'-biphenyl)-1-propyl ester
optically active 4-nonylcyclohexylcarboxylic acid 1-(4-hexyl-4'-biphenylyl)-1-propyl ester
optically active 4-decylcyclohexylcarboxylic acid 1-(4-ethyl-4'-biphenylyl)-1-propyl ester
optically active 4-methylbiphenylyl-4'-carboxylic acid 1-phenyl-1-propyl ester
optically active 4-ethylbiphenyl-4'-carboxylic acid 1-phenyl-1-propyl ester
optically active 4-propylbiphenyl-4'-carboxylic acid 1-phenyl-1-propyl ester
optically active 4-butylbiphenyl-4'-carboxylic acid 1-phenyl-1-propyl ester
optically active 4-pentylbiphenyl-4'-carboxylic acid 1-phenyl-1-propyl ester
optically active 4-hexylbiphenyl-4'-carboxylic acid 1-phenyl-1-propyl ester
optically active 4-ethylbiphenyl-4'-carboxylic acid 1-(4-pentylphenyl)-1-propyl ester
optically active 4-octyloxybiphenyl-4'-carboxylic acid 1-phenyl-1-propyl ester (Example 1)
optically active 4-ethyloxybiphenyl-4'-carboxylic acid 1-(4-pentylphenyl)-propyl ester
optically active 4-propylbiphenyl-4'-carboxylic acid 1-(4-pentyloxyphenyl)-1-propyl ester
optically active 4-propyloxybiphenyl-4'-carboxylic acid 1-(4-ethylphenyl)-propyl ester
optically active 4-pentylbiphenyl-4'-carboxylic acid 1-(4-hexylphenyl)-1-propyl ester
optically active 4-hexylbiphenyl-4'-carboxylic acid 1-(4-hexyloxyphenyl)-1-propyl ester
optically active 4-heptylbiphenyl-4'-carboxylic 1-(4-methylphenyl)-1-propyl ester
optically active 4-heptyloxybiphenyl-4'-carboxylic acid 1-(4-methyloxyphenyl)-1-propyl ester
optically active 4-octylbiphenyl-4'-carboxylic acid 1-(4-propylphenyl)-1-propyl ester
optically active 2-ethylpyrimidine-5-carboxylic acid 1-phenyl-1-propyl ester
optically active 2-propylpyrimidine-5-carboxylic acid 1-phenyl-1-propyl ester
optically active 2-pentylpyrimidine-5-carboxylic acid 1-phenyl-1-propyl ester
optically active 2-propyloxypyrimidine-5-carboxylic acid 1-phenyl-1-propyl ester
optically active 2-pentyloxypyrimidine-5-carboxylic acid 1-phenyl-1-propyl ester
optically active 2-nonylpyrimidine-5-carboxylic acid 1-phenyl-1-propyl ester
optically active 2-propylpyrimidine-5-carboxylic acid 1-(4-methylphenyl)-1-propyl ester
optically active 2-pentylpyrimidine-5-carboxylic acid 1-(4-ethylphenyl)-1-propyl ester
optically active 2-pentyloxypyrimidine-5-carboxylic acid 1-(4-propylphenyl)-1-propyl ester
optically active 2-hexylpyrimidine-5-carboxylic acid 1-(4-ethylphenyl)-1-propyl ester
optically active 2-heptylpyrimidine-5-carboxylic acid 1-(4-pentylphenyl)-1-propyl ester
optically active 2-octylpyrimidine-5-carboxylic acid 1-(4-hexylphenyl)-1-propyl ester
optically active 2-nonylpyrimidine-5-carboxylic acid 1-(4-nonylphenyl)-1-propyl ester
optically active 5-ethylpyrimidine-2-carboxylic acid 1-phenyl-1-propyl ester
optically active 5-propylpyrimidine-2-carboxylic acid 1-phenyl-1-propyl ester
optically active 5-pentylpyrimidine-2-carboxylic acid 1-phenyl-1-propyl ester
optically active 5-propyloxypyrimidine-2-carboxylic acid 1-phenyl-1-propyl ester optically active 5-pentyloxypyrimidine-2-carboxylic acid 1-phenyl-1-propyl ester
optically active 5-nonylpyrimidine-2-carboxylic acid 1-phenyl-1-propyl ester
optically active 5-propylpyrimidine-2-carboxylic acid 1-(4-methylphenyl)-1-propyl ester
optically active 5-pentylpyrimidine-2-carboxylic acid 1-(4-ethylphenyl)-1-propyl ester
optically active 5-pentyloxypyrimidine-2-carboxylic acid 1-(4-propylphenyl)-1-propyl ester
optically active 5-hexylpyrimidine-2-carboxylic acid 1-(4-ethylphenyl)-1-propyl ester
optically active 5-heptylpyrimidine-2-carboxylic acid 1-(4-pentylphenyl)-1-propyl ester
optically active 5-octylpyrimidine-2-carboxylic acid 1-(4-hexylphenyl)-1-propyl ester
optically active 5-nonylpyrimidine-2-carboxylic acid 1-(4-nonylphenyl)-1-propyl ester
optically active 2-ethylpyridine-5-carboxylic acid 1-phenyl-1-propyl ester
optically active 2-propylpyridine-5-carboxylic acid 1-phenyl-1-propyl ester
optically active 2-propyloxypyridine-5-carboxylic acid 1-phenyl-1-propyl ester
optically active 2-pentyloxypyridine-5carboxylic acid 1-phenyl-1-propyl ester
optically active 2-nonylpyridine-5-carboxylic acid 1-phenyl-1-propyl ester
optically active 2-propylpyridine-5-carboxylic acid 1-(4-methylphenyl)-1-propyl ester
optically active 2-pentylpyridine-5-carboxylic acid 1-(4-ethylphenyl)-1-propyl ester
optically active 2-pentyloxypyridine-5-carboxylic acid 1-(4-propylphenyl)-1-propyl ester
optically active 2-hexylpyridine-5-carboxylic acid 1-(4-ethylphenyl)-1-propyl ester
optically active 2-heptylpyridine-5-carboxylic acid 1-(4-pentylphenyl)-1-propyl ester
optically active 2-octylpyridine-5-carboxylic acid 1-(4-hexylphenyl)-1-propyl ester
optically active 2-nonylpyridine-5-carboxylic acid 1-(4-nonylphenyl)-1-propyl ester
optically active 5-ethylpyridine-2-carboxylic acid 1-phenyl-1-propyl ester
optically active 5-propylpyridine-2-carboxylic acid 1-phenyl-1-propyl ester
optically active 5-pentylpyridine-2-carboxylic acid 1-phenyl-1-propyl ester
optically active 5-propyloxypyridine-2-carboxylic acid 1-phenyl-1-propyl ester
optically active 5-pentyloxypyridine-2-carboxylic acid 1-phenyl-1-propyl ester
optically active 5-nonylpyridine-2-carboxylic acid 1-phenyl-1-propyl ester
optically active 5-propylpyridine-2-carboxylic acid 1-(4-methylphenyl)-1-propyl ester
optically active 5-pentylpyridine-2-carboxylic acid 1-(4-ethylphenyl)-1-propyl ester
optically active 5-pentyloxypyridine-2-carboxylic acid 1-(4-propylphenyl)-1-propyl ester
optically active 5-hexylpyridine-2-carboxylic acid 1-(4-ethylphenyl)-1-propyl ester
optically active 5-heptylpyridine-2-carboxylic acid 1-(4-pentylphenyl)-1-propyl ester
optically active 5-octylpyridine-2-carboxylic acid 1-(4-hexylphenyl)-1-propyl ester
optically active 5-nonylpyridine-2-carboxylic acid 1-(4-nonylphenyl)-1-propyl ester
optically active 1-(4-methylphenyl)-1-propanol
optically active 1-(4-ethylphenyl)-1-propanol
optically active 1-(4-propylphenyl)-1-propanol
optically active 1-(4-butylphenyl)-1-propanol
optically active 1-(4-pentylphenyl)-1-propanol
optically active 1-(4-hexylphenyl)-1-propanol
optically active 1-(4-heptylphenyl)-1-propanol
optically active 1-(4-octylphenyl)-1-propanol
optically active 1-(4-nonylphenyl)-1-propanol
optically active 1-(4-decylphenyl)-1-propanol
optically active 1-(4-undecylphenyl)-1-propanol
optically active 1-(4-dodecylphenyl)-1-propanol
optically active 1-(4-chlorophenyl)-1-propanol
optically active 1-(4-bromophenyl)-1-propanol
optically active 1-(4-fluorophenyl)-1-propanol
optically active 1-(4-cyanophenyl)-1-propanol
optically active 1-(4-methyloxyphenyl)-1-propanol
optically active 1-(4-ethyloxyphenyl)-1-propanol
optically active 1-(4-propyloxyphenyl)-1-propanol
optically active 1-(4-butyloxyphenyl)-1-propanol
optically active 1-(4-pentyloxyphenyl)-1-propanol
optically active 1-(4-hexyloxyphenyl)-1-propanol
optically active 1-(4-heptyloxyphenyl)-1-propanol
optically active 1-(4-octyloxyphenyl)-1-propanol
optically active 1-(4-nonyloxyphenyl)-1-propanol
optically active 1-(4-decyloxyphenyl)-1-propanol
optically active 1-(4-undecyloxyphenyl)-1-propanol
optically active 1-(4-dodecyloxyphenyl)-1-propanol
optically active 1-(4-chlorophenyl)-1-propanol
optically active 1-(4-bromophenyl)-1-propanol
optically active 1-(4-fluorophenyl)-1-propanol
optically active 1-(4-cyanophenyl)-1-propanol
optically active 1-(4-methyl-4'-biphenylyl)-1-propanol
optically active 1-(4-ethyl-4'-biphenylyl)-1-propanol
optically active 1-(4-propyl-4'-biphenylyl)-1-propanol
optically active 1-(4-butyl-4'-biphenylyl)-1-propanol
optically active 1-(4-pentyl-4'-biphenylyl)-1-propanol
optically active 1-(4-hexyl-4'-biphenylyl)-1-propanol
optically active 1-(4-heptyl-4'-biphenylyl)-1-propanol
optically active 1-(4-octyl-4'-biphenylyl)-1-propanol
optically active 1-(4-nonyl-4'-biphenylyl)-1-propanol
optically active 1-(4-methyloxy-4'-biphenylyl)-1-propanol
optically active 1-(4-ethyloxy-4'-biphenylyl)-1-propanol
optically active 1-(4-propyloxy-4'-biphenylyl)-1-propanol
optically active 1-(4-butyloxy-4'-biphenylyl)-1-propanol
optically active 1-(4-pentyloxy-4'-biphenylyl)-1-propanol
optically active 1-(4-hexyloxy-4'-biphenylyl)-1-propanol
optically active 1-(4-heptyloxy-4'-biphenylyl)-1-propanol
optically active 1-{4-(2-methylpyrimid-5-ylphenyl)}-1-propanol
optically active 1-{4-(2-ethylpyrimid-5-ylphenyl)}-1-propanol
optically active 1-{4-(2-propylpyrimid-5-ylphenyl)}-1-propanol
optically active 1-{4-(2-butylpyrimid-5-ylphenyl)}-1-propanol
optically active 1-{4-(2-pentylpyrimid-5-ylphenyl}-1-propanol optically active 1-{4-(2-hexylpyrimid-5-ylphenyl}-1-propanol
optically active 1-{4-(2-heptylpyrimid-5-ylphenyl}-1-propanol
optically active 1-{4-(2-octylpyrimid-5-ylphenyl)}-1-propanol
optically active 1-{4-(2-nonylpyrimid-5-ylphenyl)}-1-propanol
optically active 1-{4-(2-decylpyrimid-5-ylphenyl)}-1-propanol
optically active 1-{4-(2-methyloxypyrimid-5-ylphenyl)}-1-propanol
optically active 1-{4-(2-ethyloxypyrimid-5-ylphenyl)}-1-propanol
optically active 1-{4-(2-propyloxypyrimid-5-ylphenyl)}-1-propanol
optically active 1-{4-(2-butyloxypyrimid-5-ylphenyl)}-1-propanol
optically active 1-{4-(2-pentyloxypyrimid-5-ylphenyl)}-1-propanol
optically active 1-{4-(2-hexyloxypyrimid-5-ylphenyl)}-1-propanol
optically active 1-{4-(2-heptyloxypyrimid-5-ylphenyl)}-1-propanol
optically active 1-{4-(2-octyloxypyrimid-5-ylphenyl)}-1-propanol
optically active 1-{4-(2-nonyloxypyrimid-5-ylphenyl)}-1-propanol
optically active 1-{4-(2-decyloxypyrimid-5-ylphenyl)}-1-propanol
optically active 1-{4-(5-methylpyrimid-2-ylphenyl)}-1-propanol
optically active 1-{4-(5-ethylpyrimid-2-ylphenyl)}-1-propanol
optically active 1-{4-(5-propylpyrimid-2-ylphenyl)}-1-propanol
optically active 1-{4-(5-butylpyrimid-2-ylphenyl)}-1-propanol
optically active 1-{4-(5-pentylpyrimid-2-ylphenyl)}-1-propanol
optically active 1-{4-(5-hexylpyrimid-2-ylphenyl)}-1-propanol
optically active 1-{4-(5-heptylpyrimid-2-ylphenyl)}-1-propanol
optically active 1-{4-(5-octylpyrimid-2-ylphenyl)}-1-propanol
y active 1-{4-(5-nonylpyrimid-2-ylphenyl)}-1-propanol
optically active 1-{4-(5-decylpyrimid-2-ylphenyl)}-1-propanol
optically active 1-{4-(5-methyloxypyrimid-2-ylphenyl)}-1-propanol
optically active 1-{4-(5-ethyloxypyrimid-2-ylphenyl)}-1-propanol
optically active 1-{4-(5-propyloxypyrimid-2-ylphenyl)}-1-propanol
optically active 1-{4-(5-butyloxypyrimid-2-ylphenyl)}-1-propanol
optically active 1-{4-(5-pentyloxypyrimid-2-ylphenyl)}-1-propanol
optically active 1-{4-(5-hexyloxypyrimid-2-ylphenyl)}-1-propanol
optically active 1-{4-(5-heptyloxypyrimid-2-ylphenyl)}-1-propanol
optically active 1-{4-(5-octyloxypyrimid-2-ylphenyl)}-1-propanol
optically active 1-{4-(5-nonyloxypyrimid-2-ylphenyl)}-1-propanol
optically active 1-{4-(5-decyloxypyrimid-2-ylphenyl)}-1-propanol
optically active 1-{4-(2-methylpyrid-5-ylphenyl)}-1-propanol
optically active 1-{4-(2-ethylpyrid-5-ylphenyl)}-1-propanol
optically active 1-{4-(2-propylpyrid-5-ylphenyl)}-1-propanol
optically active 1-{4-(2-butylpyrid-5-ylphenyl)}-1-propanol
optically active 1-{4-(2-pentylpyrid-5-ylphenyl)}-1-propanol
optically active 1-{4-(2-hexylpyrid-5-ylphenyl)}-1-propanol
optically active 1-{4-(2-heptylpyrid-5-ylphenyl)}-1-propanol
optically active 1-{4-(2-octylpyrid-5-ylphenyl)}-1-propanol
optically active 1-{4-(2-nonylpyrid-5-ylphenyl)}-1-propanol
optically active 1-{4-(2-decylpyrid-5-ylphenyl)}-1-propanol
optically active 1-{4-(2-methyloxypyrid-5-ylphenyl)}-1-propanol
optically active 1-{4-(2-ethyloxypyrid-5-ylphenyl)}-1-propanol
optically active 1-{4-(2-propyloxypyrid-5-ylphenyl)}-1-propanol
optically active 1-{4-(2-butyloxypyrid-5-ylphenyl)}-1-propanol
optically active 1-{4-(2-pentyloxypyrid-5-ylphenyl)}-1-propanol
optically active 1-{4-(2-hexyloxypyrid-5-ylphenyl)}-1-propanol
optically active 1-{4-(2-heptyloxypyrid-5-ylphenyl)}-1-propanol
optically active 1-{4-(2-octyloxypyrid-5-ylphenyl)}-1-propanol
optically active 1-{4-(2-nonyloxypyrid-5-ylphenyl)}-1-propanol
optically active 1-{4-(2-decyloxypyrid-5-ylphenyl)}-1-propanol
optically active 1-{4-(5-methylpyrid-2-ylphenyl)}-1-propanol
optically active 1-{4-(5-ethylpyrid-2-ylphenyl)}-1-propanol
optically active 1-{4-(5-propylpyrid-2-ylphenyl)}-1-propanol
optically active 1-{4-(5-butylpyrid-2-ylphenyl)}-1-propanol
optically active 1-{4-(5-pentylpyrid-2-ylphenyl)}-1-propanol
optically active 1-{4-(5-hexylpyrid-2-ylphenyl)}-1-propanol
optically active 1-{4-(5-heptylpyrid-2-ylphenyl)}-1-propanol
optically active 1-{4-(5-octylpyrid-2-ylphenyl)}-1-propanol
optically active 1-{4-(5-nonylpyrid-2-ylphenyl)}-1-propanol
optically active 1-{4-(5-decylpyrid-2-ylphenyl)}-1-propanol
optically active 1-{4-(5-methyloxypyrid-2-ylphenyl)}-1-propanol
optically active 1-{4-(5-ethyloxypyrid-2-ylphenyl)}-1-propanol
optically active 1-{4-(5-propyloxypyrid-2-ylphenyl)}-1-propanol optically active 1-{4-(5-butyloxypyrid-2-ylphenyl)}-1-propanol
optically active 1-{4-(5-pentyloxypyrid-2-ylphenyl)}-1-propanol
optically active 1-{4-(5-hexyloxypyrid-2-ylphenyl)}-1-propanol
optically active 1-{4-(5-heptyloxypyrid-2-ylphenyl)}-1-propanol
optically active 1-{4-(5-octyloxypyrid-2-ylphenyl)}-1-propanol
optically active 1-{4-(5-nonyloxypyrid-2-ylphenyl)}-1-propanol
optically active 1-{4-(5-decyloxypyrid-2-ylphenyl)}-1-propanol
optically active 1-{4-(4-methylcyclohexyl)phenyl}-1-propanol
optically active 1-{4-(4-ethylcyclohexyl)phenyl}-1-propanol
optically active 1-{4-(4-propylcyclohexyl)phenyl}-1-propanol
optically active 1-{4-(4-butylcyclohexyl)phenyl}-1-propanol
optically active 1-{4-(4-pentylcyclohexyl)phenyl}-1-propanol
optically active 1-{4-(4-hexylcyclohexyl)phenyl}-1-propanol
optically active 1-{4-(4-heptylcyclohexyl)phenyl}-1-propanol
optically active 1-{4-(4-octylcyclohexyl)phenyl}-1-propanol
optically active 1-{4-(4-nonylcyclohexyl)phenyl}-1-propanol
optically active 1-{4-(4-decylcyclohexyl)phenyl}-1-propanol
optically active 1-{4-(4-methyloxycyclohexyl)phenyl}-1-propanol
optically active 1-{4-(4-ethyloxycyclohexyl)phenyl}-1-propanol
optically active 1-{4-(4-propyloxycyclohexyl)1phenyl}-1-propanol
optically active 1-{4-(4-butyloxycyclohexyl)phenyl}-1-propanol
optically active 1-{4-(4-pentyloxycyclohexyl)phenyl}-1-propanol
optically active 1-{4-(4-hexyloxycyclohexyl)phenyl}-1-propanol
optically active 1-{4-(4-heptyloxycyclohexyl)phenyl}-1-propanol
optically active 1-{4-(4-octyloxycyclohexyl)phenyl}-1-propanol
optically active 1-{4-(4-nonyloxycyclohexyl)phenyl}-1-propanol
optically active 1-{4-(4-decyloxycyclohexyl)phenyl}-1-propanol

PREPARATION OF THE COMPOUND

The compound of the formula (I) of the present invention may be suitably prepared for example by way of the following route:

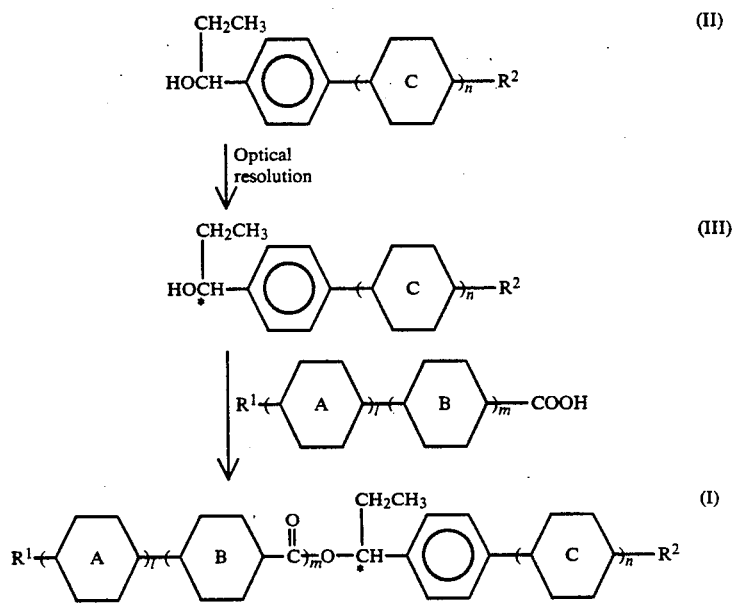

wherein $R^1$, $R^2$, l, m, n,

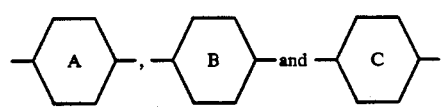

each are as defined above.

Namely, a 1-substituted propanol as a racemate expressed by the formula (II) is optically resolved to selectively obtain S-form and R-form, followed by reacting therewith a carboxylic acid expressed by the formula (III) to obtain the compound of the formula (I).

The compound of the present invention will be described in more detail by way of Examples.

EXAMPLE 1

Preparation of R-(-)-4-octyloxybiphenyl-4'-carboxylic acid 1-phenyl-1-propyl ester (a compound of the formula (I) wherein $R^1=CH_3(CH_2)_7-O-$, $R^2$=hydrogen atom, l=m=1 and n=0)

FIRST STEP

Preparation of optically active 1-phenyl-1-propanol

A mixture of (±)-1-phenyl-1-propanol (40.9 g), tributyrin (99.8 g) and lipase P (15 g) was agitated at 35° C. for 502 hours, followed by filtering off lipase P and subjecting the residue to vacuum distillation to obtain S-(-)-1-phenyl-1-propanol (19.9 g). bp: 71.8° C./2.5 mmHg, $[\alpha]_D^{24.8} = -14.4°$ (neat).

Further, a fraction of bp 101.3° C./2.6 mmHg was subjected to hydrolysis reaction in a conventional manner to obtain R-(+)-1-phenyl-1-propanol (10.2 g). $[\alpha]_D^{24.7} = +25.8°$ (neat).

SECOND STEP

Preparation of the captioned compound

A mixture of R-(+)-1-phenyl-1-propanol (5.5 g) prepared in the first step, 4-octyloxy-4'-carboxylic acid (15 g), 4,4'-dicyclohexylcarbodiimide (9.5 g), 4-dimethylaminopyridine (0.6 g) and dichloromethane (90 ml) was agitated at room temperature for 2 hours, followed by filtering off the resulting insolubles, distilling off dichloromethane, purifying the residue according to column chromatography using toluene as a solvent and twice recrystallizing the resulting substance from ethanol to obtain R-(-)-4-octyloxy-biphenyl-4'-carboxylic acid 1-phenyl-1-propyl ester. Mp 53.5-54.3° C., $[\alpha]_D^{25.0} = -87.3°$ (C=1.15, CHCl$_3$).

Further, this product was confirmed to well accord with the captioned compound according to elemental analysis, NMR spectra and IR spectra.

EXAMPLE 2 (Use example 1)

The compound of Example 1 of the present invention, i.e.

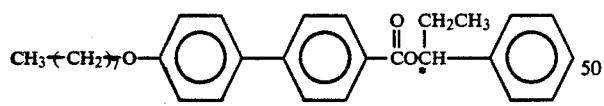

was added in an amount 1% by weight to a nematic liquid crystal composition (a commercially available ZLI-1132 made by Merck Company) to prepare a chiral nematic liquid crystal composition. This composition was filled in a wedge-form cell, subjected to a parallel aligning treatment and the resulting cell was observed under a polarizing microscope. As a result, the following helical pitches were observed:

| Temperature T (°C.) | 20 | 25 | 30 | 40 | 50 | 60 |
|---|---|---|---|---|---|---|
| Pitch (μm) | 3.7 | 3.7 | 3.7 | 3.7 | 3.8 | 3.8 |
| length $\delta_{p20-T}$ | — | — | 0 | 0 | 0.089 | 0 |

"$\delta_{p20-T}$" in the above Table refers to a parameter expressing the temperature characteristic and is defined by the following equation:

$$\delta_{p20-T} = \frac{2(p(20) - p(T))}{p(20) + p(T)} \times \frac{100}{20 - T}$$

In this equation,
p(20) pitch length at 20° C.
p(T): pitch length at T° C.

As described above, the exhibited pitch length is very short and further, there is almost no change in the pitch with temperature rise. Thus, it was confirmed that the compound of the present invention is a superior pitch-adjusting agent for liquid crystal compositions.

What we claim is:

1. An optically active compound expressed by the formula

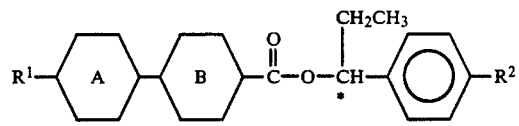

wherein $R^1$ and $R^2$ each represent alkyl or alkoxy each of 1 to 20 carbon atoms, halogen or hydrogen, and

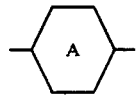

and

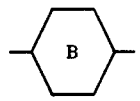

each represent

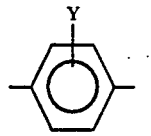

wherein Y represents hydrogen, halogen or cyano.

2. A liquid crystal composition comprising at least two components at least one of which is an optically active compound as set forth in claim 1.

3. An electro optical element containing a liquid crystal composition comprising at least two components at least one of which is an optically active compound as set forth in claim 1.

* * * * *